(12) United States Patent
Patton

(10) Patent No.: US 7,300,919 B2
(45) Date of Patent: *Nov. 27, 2007

(54) PULMONARY DELIVERY OF ACTIVE FRAGMENTS OF PARATHYROID HORMONE

(75) Inventor: John S. Patton, San Carlos, CA (US)

(73) Assignee: Nektar Therapeutics, San Carlos, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 10/245,707

(22) Filed: Sep. 18, 2002

(65) Prior Publication Data

US 2003/0171282 A1    Sep. 11, 2003

Related U.S. Application Data

(60) Continuation of application No. 09/577,264, filed on May 22, 2000, which is a continuation of application No. 09/128,401, filed on Aug. 3, 1998, now Pat. No. 6,080,721, which is a division of application No. 08/625,586, filed on Mar. 28, 1996, now Pat. No. 5,814,607, which is a continuation of application No. 08/232,849, filed on Apr. 25, 1994, now Pat. No. 5,607,915, which is a continuation of application No. 07/953,397, filed on Sep. 29, 1992, now abandoned.

(51) Int. Cl.
*A61K 38/29* (2006.01)

(52) U.S. Cl. .................. 514/12; 530/324; 530/399; 424/45; 424/469; 424/489

(58) Field of Classification Search .................. 514/12; 530/324, 399; 424/45, 469, 489
See application file for complete search history.

(56) References Cited

U.S. PATENT DOCUMENTS

| | | | |
|---|---|---|---|
| 979,993 A | 12/1910 | O'Byrne et al. |
| 1,855,591 A | 4/1932 | Wallenstein |
| 2,457,036 A | 12/1948 | Epstein |
| 3,362,405 A | 1/1968 | Hazel |
| 3,557,717 A | 1/1971 | Chivers |
| 3,619,294 A | 11/1971 | Black et al. |
| 3,632,357 A | 1/1972 | Childs |
| 3,655,442 A | 4/1972 | Schwer et al. |
| 3,745,682 A | 7/1973 | Waldeisen |
| 3,937,668 A | 2/1976 | Zolle |
| 3,948,263 A | 4/1976 | Drake, Jr. et al. |
| 3,964,483 A | 6/1976 | Mathes |
| 4,036,223 A | 7/1977 | Obert |
| 4,098,273 A | 7/1978 | Glenn |
| 4,102,999 A | 7/1978 | Umezawa et al. |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,180,593 A | 12/1979 | Cohan |
| 4,211,769 A | 7/1980 | Okada et al. |
| 4,244,949 A | 1/1981 | Gupta |
| 4,253,468 A | 3/1981 | Lehmbeck |
| 4,326,524 A | 4/1982 | Drake, Jr. et al. |
| 4,327,076 A | 4/1982 | Puglia et al. |
| 4,327,077 A | 4/1982 | Puglia et al. |
| 4,371,557 A | 2/1983 | Oppy et al. |
| 4,407,786 A | 10/1983 | Drake et al. |
| 4,452,239 A | 6/1984 | Malem |
| 4,484,577 A | 11/1984 | Sackner et al. |
| 4,534,343 A | 8/1985 | Nowacki et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,656,250 A * | 4/1987 | Morita et al. ............... 530/324 |
| 4,659,696 A | 4/1987 | Hirai et al. |
| 4,680,027 A | 7/1987 | Parsons et al. |
| 4,684,719 A | 8/1987 | Nishikawa et al. |
| 4,698,328 A | 10/1987 | Neer et al. ................... 514/12 |
| 4,701,417 A | 10/1987 | Portenhauser et al. |
| 4,713,249 A | 12/1987 | Schroder et al. |

(Continued)

FOREIGN PATENT DOCUMENTS

DE    471490    8/1931

(Continued)

OTHER PUBLICATIONS

Young Paul M., International journal of pharmaceutics, (May 30, 2005) 296 (1-2) 26-33.*

(Continued)

*Primary Examiner*—David Lukton
(74) *Attorney, Agent, or Firm*—Fish & Richardson P.C.

(57) ABSTRACT

Systemic delivery of parathyroid hormone to a mammalian host is accomplished by inhalation through the mouth of a dispersion of an N-terminal fragment of PTH. It has been found that such respiratory delivery of the PTH fragment provides a pulsatile concentration profile of the PTH in the host's serum. PTH fragment compositions include dry powder formulations having the PTH present in a dry bulking powder, liquid solutions or suspensions suitable for nebulization, and aerosol propellants suitable for use in a metered dose inhaler.

6 Claims, 1 Drawing Sheet

U.S. PATENT DOCUMENTS

| | | | |
|---|---|---|---|
| 4,721,709 A | 1/1988 | Seth et al. | |
| 4,739,754 A | 4/1988 | Shaner | |
| 4,758,583 A | 7/1988 | Cerami et al. | |
| 4,761,400 A | 8/1988 | Doat et al. | |
| 4,762,857 A | 8/1988 | Bollin, Jr. et al. | |
| 4,790,824 A | 12/1988 | Morrow et al. | |
| 4,793,997 A | 12/1988 | Drake et al. | |
| 4,812,444 A | 3/1989 | Mitsuhashi et al. | |
| 4,814,436 A | 3/1989 | Shibata et al. | |
| 4,819,629 A | 4/1989 | Jonson | |
| 4,824,938 A | 4/1989 | Koyama et al. | |
| 4,830,858 A | 5/1989 | Payne et al. | |
| 4,833,125 A | 5/1989 | Neer et al. | 514/12 |
| 4,847,079 A | 7/1989 | Kwan | |
| 4,855,326 A | 8/1989 | Fuisz | |
| 4,861,627 A | 8/1989 | Mathiowitz et al. | |
| 4,865,871 A | 9/1989 | Livesey et al. | |
| 4,866,051 A | 9/1989 | Hunt | |
| 4,883,762 A | 11/1989 | Hoskins | |
| 4,891,319 A | 1/1990 | Roser | |
| 4,895,719 A | 1/1990 | Radhakrishnan et al. | |
| 4,906,463 A | 3/1990 | Cleary et al. | |
| 4,907,583 A | 3/1990 | Wetterlin et al. | |
| 4,942,544 A | 7/1990 | McIntosh et al. | |
| 4,952,402 A | 8/1990 | Sparks et al. | |
| 4,984,158 A | 1/1991 | Hillsman | |
| 4,988,683 A | 1/1991 | Corbiere | |
| 5,006,343 A | 4/1991 | Benson et al. | |
| 5,011,678 A | 4/1991 | Wang et al. | 424/45 |
| 5,013,557 A | 5/1991 | Tai | |
| 5,017,372 A | 5/1991 | Hastings | |
| 5,026,566 A | 6/1991 | Roser | |
| 5,026,772 A | 6/1991 | Kobayashi et al. | |
| 5,033,463 A | 7/1991 | Cocozza | |
| 5,043,165 A | 8/1991 | Radhakrishnan | |
| 5,049,388 A | 9/1991 | Knight et al. | |
| 5,049,389 A | 9/1991 | Radhakrishnan | |
| 5,059,587 A * | 10/1991 | Yamamoto et al. | 514/12 |
| 5,089,181 A | 2/1992 | Hauser | |
| 5,098,893 A | 3/1992 | Franks et al. | |
| 5,112,596 A | 5/1992 | Malfroy-Camine | |
| 5,112,598 A | 5/1992 | Bielsalski | |
| 5,113,855 A | 5/1992 | Newhoe | |
| 5,149,653 A | 9/1992 | Roser | |
| 5,160,745 A | 11/1992 | DeLuca et al. | |
| 5,173,298 A | 12/1992 | Meadows et al. | |
| 5,182,097 A | 1/1993 | Byron et al. | |
| 5,200,399 A | 4/1993 | Wettlaufer et al. | |
| 5,202,333 A | 4/1993 | Berger et al. | |
| 5,204,108 A | 4/1993 | Illum | |
| 5,215,079 A | 6/1993 | Fine et al. | |
| 5,225,183 A | 7/1993 | Purewal et al. | |
| 5,230,884 A | 7/1993 | Evans et al. | 424/45 |
| 5,239,993 A | 8/1993 | Evans | |
| 5,240,712 A | 8/1993 | Smith | |
| 5,240,843 A | 8/1993 | Gibson et al. | |
| 5,240,846 A | 8/1993 | Collins et al. | |
| 5,254,330 A | 10/1993 | Ganderton et al. | |
| 5,260,306 A | 11/1993 | Boardman et al. | |
| 5,270,048 A | 12/1993 | Drake | |
| 5,284,656 A | 2/1994 | Platz et al. | |
| 5,290,765 A | 3/1994 | Wettlaufer et al. | |
| 5,302,581 A | 4/1994 | Savin et al. | 514/12 |
| 5,306,506 A | 4/1994 | Zema et al. | |
| 5,309,900 A | 5/1994 | Knoch et al. | |
| 5,312,335 A | 5/1994 | McKinnon et al. | |
| 5,312,909 A | 5/1994 | Driessen et al. | |
| 5,342,625 A | 8/1994 | Hauer et al. | |
| 5,348,852 A | 9/1994 | Bonderman | |
| 5,354,562 A | 10/1994 | Platz et al. | |
| 5,354,934 A | 10/1994 | Pitt et al. | |
| 5,366,734 A | 11/1994 | Hutchinson | |
| 5,376,386 A | 12/1994 | Ganderton et al. | |
| 5,380,473 A | 1/1995 | Bogue et al. | |
| 5,384,133 A | 1/1995 | Boyes et al. | |
| 5,387,431 A | 2/1995 | Fuisz | |
| 5,403,861 A | 4/1995 | Goldwin et al. | |
| 5,404,871 A | 4/1995 | Goodman et al. | |
| 5,422,360 A | 6/1995 | Miyajima et al. | |
| 5,422,384 A | 6/1995 | Samuels et al. | |
| 5,425,951 A | 6/1995 | Goodrich, Jr. et al. | |
| 5,453,514 A | 9/1995 | Niigata et al. | |
| 5,458,135 A | 10/1995 | Patton et al. | 128/200.14 |
| 5,482,927 A | 1/1996 | Maniar et al. | |
| 5,512,547 A | 4/1996 | Johnson et al. | |
| 5,518,709 A | 5/1996 | Sutton et al. | |
| 5,547,696 A | 8/1996 | Sorensen | |
| 5,563,122 A | 10/1996 | Endo et al. | 514/12 |
| 5,567,439 A | 10/1996 | Myers et al. | |
| 5,571,499 A | 11/1996 | Hafler et al. | |
| 5,578,567 A | 11/1996 | Cardinaux et al. | 514/12 |
| 5,580,859 A | 12/1996 | Felgner et al. | |
| 5,589,167 A | 12/1996 | Cleland et al. | |
| 5,591,453 A | 1/1997 | Ducheyne et al. | |
| 5,607,915 A * | 3/1997 | Patton | 514/12 |
| 5,611,344 A | 3/1997 | Bernstein et al. | |
| 5,618,786 A | 4/1997 | Roosdorp et al. | |
| 5,621,094 A | 4/1997 | Roser et al. | |
| 5,631,225 A | 5/1997 | Sorensen | |
| 5,642,728 A | 7/1997 | Andersson et al. | |
| 5,654,278 A | 8/1997 | Sorensen | |
| 5,681,746 A | 10/1997 | Bodner et al. | |
| 5,705,482 A | 1/1998 | Christensen et al. | |
| 5,707,644 A | 1/1998 | Illum | |
| 5,728,574 A | 3/1998 | Legg | |
| 5,733,555 A | 3/1998 | Chu | |
| 5,766,520 A | 6/1998 | Bronshtein | |
| 5,775,320 A | 7/1998 | Patton et al. | |
| 5,780,014 A | 7/1998 | Eljamal et al. | |
| 5,780,295 A | 7/1998 | Livesey et al. | |
| 5,814,607 A * | 9/1998 | Patton | 514/12 |
| 5,849,700 A | 12/1998 | Sorensen et al. | |
| 5,851,453 A | 12/1998 | Hanna et al. | |
| 5,891,873 A | 4/1999 | Colaco et al. | |
| 5,928,469 A | 7/1999 | Franks et al. | |
| 5,948,411 A | 9/1999 | Koyama et al. | |
| 5,955,448 A | 9/1999 | Colaco et al. | |
| 5,972,366 A | 10/1999 | Haynes et al. | |
| 5,976,436 A | 11/1999 | Livesley et al. | |
| 5,993,783 A | 11/1999 | Eljamal et al. | |
| 5,993,805 A | 11/1999 | Sutton et al. | |
| 5,994,314 A | 11/1999 | Eljamal et al. | |
| 5,997,848 A | 12/1999 | Patton et al. | |
| 6,013,638 A | 1/2000 | Crystal et al. | |
| 6,019,968 A | 2/2000 | Platz et al. | |
| 6,034,080 A | 3/2000 | Colaco et al. | |
| 6,051,256 A | 4/2000 | Platz et al. | |
| 6,060,069 A | 5/2000 | Hill et al. | |
| 6,071,428 A | 6/2000 | Franks et al. | |
| 6,077,543 A | 6/2000 | Gordon et al. | |
| 6,080,721 A * | 6/2000 | Patton | 514/12 |
| 6,123,924 A | 9/2000 | Mistry et al. | |
| 6,123,936 A | 9/2000 | Platz et al. | |
| 6,136,346 A | 10/2000 | Eljamal et al. | |
| 6,138,668 A | 10/2000 | Patton et al. | |
| 6,142,216 A | 11/2000 | Lannes | |
| 6,165,463 A | 12/2000 | Platz et al. | |
| 6,187,344 B1 | 2/2001 | Eljamal et al. | |
| 6,190,859 B1 | 2/2001 | Putnak et al. | |
| 6,231,851 B1 | 5/2001 | Platz et al. | |
| 6,258,341 B1 | 7/2001 | Foster et al. | |
| 6,290,991 B1 * | 9/2001 | Roser et al. | 424/502 |
| 6,303,581 B2 | 10/2001 | Pearlman | |
| 6,303,582 B1 | 10/2001 | Eljamal et al. | |

| | | | | | |
|---|---|---|---|---|---|
| 6,309,671 B1 | 10/2001 | Foster et al. | EP | 0251631 | 1/1988 |
| 6,313,102 B1 | 11/2001 | Colaco et al. | EP | 0257956 | 3/1988 |
| 6,331,310 B1 | 12/2001 | Roser et al. | EP | 0282179 | 9/1988 |
| 6,344,182 B1 | 2/2002 | Sutton et al. | EP | 0325936 | 8/1989 |
| 6,358,530 B1 | 3/2002 | Eljamal et al. | EP | 0356154 | 2/1990 |
| 6,365,190 B1 | 4/2002 | Gordon et al. | EP | 0360340 | 3/1990 |
| 6,372,258 B1 | 4/2002 | Platz et al. | EP | 0366303 | 5/1990 |
| 6,423,334 B1 | 7/2002 | Brayden et al. | EP | 0383569 | 8/1990 |
| 6,423,344 B1 | 7/2002 | Platz et al. | EP | 0407028 | 1/1991 |
| 6,426,210 B1 | 7/2002 | Franks et al. | EP | 0415567 | 3/1991 |
| 6,468,782 B1 | 10/2002 | Tunnacliffe et al. | EP | 0430045 | 6/1991 |
| 6,479,049 B1 | 11/2002 | Platz et al. | EP | 0433679 | 6/1991 |
| 6,503,411 B1 | 1/2003 | Franks et al. | EP | 0463653 | 1/1992 |
| 6,509,006 B1 | 1/2003 | Platz et al. | EP | 0474874 | 3/1992 |
| 6,514,496 B1 | 2/2003 | Platz et al. | EP | 0520748 | 12/1992 |
| 6,518,239 B1 | 2/2003 | Kuo et al. | EP | 0257915 | 3/1993 |
| 6,565,841 B1 | 5/2003 | Niven et al. | EP | 0600730 | 6/1994 |
| 6,565,871 B2 | 5/2003 | Roser et al. | EP | 0616524 | 9/1994 |
| 6,569,406 B2 | 5/2003 | Stevenson et al. | EP | 0714905 | 6/1996 |
| 6,569,458 B1 | 5/2003 | Gombotz et al. | EP | 0303746 | 2/1998 |
| 6,572,893 B2 | 6/2003 | Gordon et al. | GB | 0821036 | 9/1959 |
| 6,582,728 B1 | 6/2003 | Platz et al. | GB | 1122284 | 8/1968 |
| 6,586,006 B2 | 7/2003 | Roser et al. | GB | 1182779 | 3/1970 |
| 6,589,560 B2 | 7/2003 | Foster et al. | GB | 1265615 | 3/1972 |
| 6,592,904 B2 | 7/2003 | Platz et al. | GB | 1288094 | 9/1972 |
| 6,630,169 B1 | 10/2003 | Bot et al. | GB | 1381588 | 1/1975 |
| 6,649,911 B2 | 11/2003 | Kawato | GB | 1477775 | 6/1977 |
| 6,655,379 B2 | 12/2003 | Clark et al. | GB | 1533012 | 11/1978 |
| 6,673,335 B1 | 1/2004 | Platz et al. | GB | 2105189 | 3/1983 |
| 6,685,967 B1 | 2/2004 | Patton et al. | GB | 2126588 | 3/1984 |
| 6,737,045 B2 | 5/2004 | Patton et al. | GB | 2206273 | 1/1989 |
| 6,737,066 B1 | 5/2004 | Moss | GB | 2248550 | 4/1992 |
| 6,752,893 B2 | 6/2004 | Frieder, Jr. | WO | 86/04095 | 7/1986 |
| 6,794,357 B1 * | 9/2004 | Backstrom et al. ............ 514/2 | WO | 87/00196 | 1/1987 |
| 6,797,258 B2 | 9/2004 | Platz et al. | WO | 87/02038 | 4/1987 |
| 6,811,792 B2 | 11/2004 | Roser et al. | WO | 87/05300 | 9/1987 |
| 6,825,031 B2 | 11/2004 | Franks et al. | WO | 88/08298 | 11/1988 |
| 6,893,657 B2 | 5/2005 | Roser et al. | WO | 89/06976 | 8/1989 |
| 6,921,527 B2 | 7/2005 | Platz et al. | WO | 89/09614 | 10/1989 |
| 2002/0127188 A1 | 9/2002 | Platz et al. | WO | 90/05182 | 5/1990 |
| 2002/0132787 A1 | 9/2002 | Eljamal et al. | WO | 90/11756 | 10/1990 |
| 2002/0192164 A1 | 12/2002 | Patton et al. | WO | 90/13285 | 11/1990 |
| 2003/0035778 A1 | 2/2003 | Platz et al. | WO | 90/13328 | 11/1990 |
| 2003/0068279 A1 | 4/2003 | Platz et al. | WO | 90/15635 | 12/1990 |
| 2003/0072718 A1 | 4/2003 | Platz et al. | WO | 91/06282 | 5/1991 |
| 2003/0086877 A1 | 5/2003 | Platz et al. | WO | 91/16038 | 10/1991 |
| 2003/0092666 A1 | 5/2003 | Eljamal et al. | WO | 91/16882 | 11/1991 |
| 2003/0113273 A1 | 6/2003 | Patton et al. | WO | 91/18091 | 11/1991 |
| 2003/0113900 A1 | 6/2003 | Tunnacliffe et al. | WO | 92/02133 | 2/1992 |
| 2003/0185765 A1 | 10/2003 | Platz et al. | WO | 92/18164 | 10/1992 |
| 2003/0198601 A1 | 10/2003 | Platz et al. | WO | 92/19243 | 11/1992 |
| 2003/0203036 A1 | 10/2003 | Gordon et al. | WO | 93/00951 | 1/1993 |
| 2003/0215512 A1 | 11/2003 | Foster et al. | WO | 93/02834 | 2/1993 |
| 2003/0215514 A1 | 11/2003 | Platz et al. | WO | 93/09832 | 5/1993 |
| 2004/0052825 A1 | 3/2004 | Roser et al. | WO | 93/10758 | 6/1993 |
| 2004/0096400 A1 | 5/2004 | Patton et al. | WO | 93/11746 | 6/1993 |
| 2004/0096401 A1 | 5/2004 | Patton et al. | WO | 93/13752 | 7/1993 |
| 2004/0219206 A1 | 11/2004 | Roser et al. | WO | 93/17663 | 9/1993 |
| 2005/0147566 A1 | 7/2005 | Fleming et al. | WO | 93/23065 | 11/1993 |
| 2005/0186143 A1 | 8/2005 | Stevenson et al. | WO | 93/23110 | 11/1993 |
| 2005/0203002 A1 | 9/2005 | Tzannis et al. | WO | 94/07514 | 4/1994 |
| | | | WO | 94/13271 | 6/1994 |
| | FOREIGN PATENT DOCUMENTS | | WO | 94/22423 | 10/1994 |
| | | | WO | 94/24263 | 10/1994 |
| EP | 0015123 | 9/1980 | WO | 95/00127 | 1/1995 |
| EP | 0072046 | 2/1983 | WO | 95/01324 | 1/1995 |
| EP | 0090356 | 10/1983 | WO | 95/06126 | 3/1995 |
| EP | 0122036 | 10/1984 | WO | 95/20979 | 8/1995 |
| EP | 0136030 | 4/1985 | WO | 95/23613 | 9/1995 |
| EP | 0139286 | 5/1985 | WO | 95/24183 | 9/1995 |
| EP | 0140489 | 5/1985 | WO | 95/31479 | 11/1995 |
| EP | 0222313 | 5/1987 | WO | 95/33488 | 12/1995 |
| EP | 0229810 | 7/1987 | WO | 96/03978 | 2/1996 |

| WO | 96/09085 | 3/1996 |
| WO | 96/27393 | 9/1996 |
| WO | 96/32096 | 10/1996 |
| WO | 96/32149 | 10/1996 |
| WO | 96/40049 | 12/1996 |
| WO | 96/40077 | 12/1996 |
| WO | 97/34689 | 9/1997 |
| WO | 97/41833 | 11/1997 |
| WO | 98/16205 | 4/1998 |
| WO | 98/24882 | 6/1998 |
| WO | 98/58989 | 12/1998 |
| WO | 01/87278 | 11/2001 |

OTHER PUBLICATIONS

English Abstract of Heubner, Klin. Wochenschrift 51, 2342-43 (1924).*
English Abstract of Igaki, N., J. Japan Diabetes Soc 34(5) 403-407, 1991.*
Beaucage and Carruthers, *Tett. Lett.* 22:1859-1862 (1981).
Habener et al., *Proc. Natl. Acad. Sci. USA* 68:2986-2991 (1971).
Harms et al., Int. Symp. on Osteoporosis, Aalborg, Abstract 232:723-724 (1987).
Hesch et al., *Calcif. Tissue Int.* 42:341-344 (1988).
Hesch et al., *Hormone Metabol. Res.* 16:559-560 (1984).
Hodsman et al., *Bone & Mineral* 9:137-152 (1990).
Hodsman et al., *Bone & Mineral* 14:67-83 (1991).
Neer et al., *Osteoporosis* 53:829-835 (1987).
Patton and Platz, *Adv. Drug Deliver. Rev.* 8:179-196 (1992).
Patton, *J. Controlled Release* 28:79-85 (1994).
Ahlneck et al., "The Molecular Basis of Moisture Effects on the Physical and Chemical Stability of Drugs in the Solid State", *State Int. J. Pharm*, 62: 87-95, 1990.
Allen and Kwan, "Determination of the Degree of Crystallinity in Solid-Solid Equilibria", *J. Pharm. Sci.* 58: 1190-1193, 1969.
Bandara et al., "Intraarticular Expression of Biologically Active Interleukin IL-Receptor-Antagonist Protein by Ex Vivo Gene Transfer", 90: 10764-10768, Nov. 1983.
Bell et al., "Dry Powder Aerosols I: A New Powder Inhalation Device", *J. Pharm. Sci.* 60(10): 1559-1564, Oct. 1971.
Byrstrom et al., "Microcalorimetry-A Novel Technique for characterization of Powders", *Respiratory Drug Delivery IV, Programs and Proceedings*, edited by Byron, Dalby and Farr:297-302, 1994.
Colaco et al., "Extraordinary Stability of Enzymes Dried in Trehalose: Simplified Molecular Biology", *Bio/Technology* 10: 1007-1011, 1992.
Crommelin et al., "Liposomes", Chapter 3, *Colloidal Drug Delivery Systems*, J. Kreuter, editor: 73-190, 1994.
D'Hondt, "Possible Approaches to Develop Vaccines Against Hepatitis A", *Vaccine* 10(Supplement 1): S48-S52, 1992.
Dalby et al., "Droplet Drying and Electrostatic Collection: A Novel Alternative to Conventional Communition Techniques", *J. Biopharm Sci.*, 3(½): 91-99, 1992.
Dose et al., "Survival in Extreme Dryness and DNA-Single-Strand Breaks", *Advances in Space Research*, 12(4): (4)221-(4)229, 1992.
During et al., "Long-Term Behavioral Recovery in Parkinsonian Rats by an HSV Vector Expressing Tyrosine Hydroxylase", *Science* 266 (5189): 1399-1403, Nov. 1994 [abstract—1 pg.].
Franks, "Freeze Drying: From Empiricism to Predictability", *Cyro-Letters*, 11: 93-110, 1990.
Franks et al., "Materials Science and the Production of Shelf-Stable Biologicals", *Pharm. Tech. Int.*: 7 pgs., Oct. 1991.
Hancock et al., "The Relationship Between the Glass Transition Temperature and the Water Content of Amorphous Pharmaceutical Solids", *Pharmaceutical Research* 11(4): 471-477, 1994.
Hickey, editor "Methods of Aerosol Particle Size characterization", *Pharmaceutical Inhalation Aerosol Technology*: 219-340.
"Immunotherapy of Malignancy by in vivo Gene Transfer into Tumors", *Hum. Gene Therapy* 3(4): 399-410, Aug. 1992 [abstract—1 pg.].
Labrude et al., "Protective Effect of Sucrose on Spray Drying of Oxyhemoglobin", *J. Pharm. Sci.* 78(3): 223-229, Mar. 1989.

MacKenzie, "Collapse During Freeze Drying-Qualitative and Quantitative Aspects", *Freeze Drying and Advanced Food Technology*, edited by Goldblith, Rey and Rothmayr: 277-307, 1975.
Makower et al., "Equilibrium Moisture Content and Crystallization of Amorphous Sucrose and Glucose", *Ag. and Food Chem.*,4(1): 72-77, Jan. 1956.
Martin et al., "States of Matter and Phase Equilibria", Chapter 4, *Physical Pharmacy, Physical Chemical Principles in the Pharmaceutical Sciences*, 3rd Edition: 69-91, 1983.
Monnier et al., "Mechanisms of Protection Against Damage Mediated by the Maillard Reaction in Aging Gerontology", 37: 152-165, 1991.
Nabel et al., "Direct Gene Transfer with DNA-Liposome Complexes in Melanoma: Expression, Biologic Activity, and Lack of Toxicity in Humans" *Proc. Nat'l. Acad. Sci. USA* 90: 11307-11311, Dec. 1993.
O'Connor et al., *Remington's Pharmaceutical Sciences*, 18th Edition, Chapter 88, "Powders": 1615-1632, 1990.
Pekarek et al., "Double-walled polymer microspheres for controlled drug release", *Nature* 367: 258-260, 1994.
Pikal, "Freeze-Drying of Proteins Part II: Formulation Selection", *BioPharm* 3(8): 26-30, Oct. 1990.
Roos, "Phase Transitions of Mixtures of Amorphous Polysaccharides and Sugars", *Biotechnology Progress* 7(1): 49-53, 1991.
Slade and Levine, "Non-Equilibrium Behavior of Small Carbohydrate-Water Systems", *Pure and Applied Chemistry*, 60(12): 1841-1864, 1988.
Slade and Levine, "The Glassy State Phenomenon in Food Molecules", *The Glassy State in Foods*, Blanshard & Lillford, editors: 35-101, 1993.
Sarkar and Moore, "Immunization of Mice Against Murine Mammary Tumor Virus Infection and Mammary Tumor Development", *Cancer Research* 38: 1468-1472, 1978.
Stribling et al., "Aerosol Gene Delivery in vivo", *Proc. Nat'l. Acad. Sci.* 89: 11277-11281, Dec. 1982.
Roscoe Stribling et al., The Mouse as a Model for Cationic Liposome-Based Aerosolized Gene Delivery J Biopharm Sci. 3:255-263 (1992).
Underwood, Stephen L. et al., A Novel Technique for the Administration of Bronchodilator Drugs Formulated as Dry Powers to the Anaesthetized Guinea Pig J. Pharm Methods 29:203-210 (1991).
Whittier, "Lactose and its Utilization: A Review", *J. Dairy Science* 27: 505-527, Jul. 1944.
Wolff et al., "Grafting Fibroblasts Genetically Modified to Produce L-Dopa in a Rat Model of Parkinson Disease", *Proc. Nat'l Acad. Sci. USA* 86: 9011-9014, Nov. 1989.
York, "Powdered Raw Materials: Characterizing Batch Uniformity", *Respiratory Drug Delivery IV, Programs and Proceedings*, edited by Byron, Dalby and Farr: 83-91, 1994.
Adjei and Gupta, "Pulmonary delivery of therapeutic peptides and proteins," *J. Controlled Release* 29:361-373 (1994).
Aldrich and Johnston, "Use of the spinning disk technique to produce monodisperse microspheres of human serum albumin for labeling with readioisotopes," *J Applied Radiation and Isotopes* 25:15-18 (1974).
Arakawa, et al., "Protein-solvent interactions in pharmaceutical formulations," *Pharmaceutical Res.* 8:285-291 (1991).
Derwent English abstract for DE 3713326, published Oct. 29, 1987, entitled "Spray dried water-dispersible granulates—prepd. from aq. concentrates contg. active ingredient and ammonium carbonate or ammonium nitrate".
Derwent English abstract for EP 315875, published May 17, 1989, entitled "Microcapsule prodn. contg. soluble protein or peptide—using mixt. of polyhdroxy-butyric acid and polyactide-co-glycolide".
English translation of Japanese Patent Publication 3-264535, published Nov. 15, 1991, entitled "Method for improving the elution properties of sparingly soluble drugs".
Graham and Pomeroy, "An in-vitro test for the duration of insulin suspension," *J Pharm Pharmcol* 36:427-30 (1984) (PubMed abstract only).
Kohler, "Aerosols for systemic treatment," Lung Suppl., pp. 677-684 (1990).

Lee and Sciarra, "Development of an aerosol dosage form containing insulin," *J. Pharmaceutical Sci.* 65:567-572 (1976).
Levine, H and L. Slade, "Water as a plasticizer: physico-chemical aspects of low-moisture polymeric systems," in Water Science Reviews (Franks, Ed. ), vol. 3: Water Dynamics, pp. 79-175 (1988).
Patent Abstracts of Japan, Japanese Patent Publication, JP 2084401, published Mar. 26, 1990, entitled "Porous fine cellulose granule".
Patton, "Deep-lung delivery of proteins," *Modern Drug Discovery* 1:19-28 (1998).
Pearlman and Nguyen, "Pharmaceutics of Protein Drugs," *J. Pharm. Pharmacol.* 44(suppl. 1): 178-185 (1992).
Schulter et al. "Pulmonary administration of human insulin in volunteers and type-1 diabetics," *Diabetes* 33 (Suppl):298 (1984).
*Spray Drying Handbook*, 5th ed., Masters, K (Ed.), New York: Longman Scientific & Technical, John Wiley & Sons, Inc., pp. 1-9, 32-33, 67-69, 491-537, 643-662 (1991).
Vidgren, M et al., "In vitro and in vivo deposition of drug particles from pressurized aerosol and dry powder inhaler," Drug Devel Indust Pharm 14:2649-2665 (1983).
White and Cakebread, "The glassy state in certain sugar-containing food products" *J. Food Technol.* 1:73-82 (1966).
Wigley et al., "Insulin across respiratory mucosae by aerosol delivery," *Diabetes* 20:552-556 (1971).
Yoshida, et al. "Absorption of insulin delivered to rabbit trachea using aerosol dosage form," J *Pharmaceutical Sci.* 68:670-671 (1979).
IUPAC Compendium of Chemical Terminology 1st Edition, 1985, pp. 258, 385.
Agrimi, U. et al., "Amyloid, Amyloid-Inducers, Cytokines and Heavy Metals in Scrapie and Other Human and Animal Subacute Spongiform Encephalopathies: Some Hypotheses", *Med. Hypotheses* 40(2): 113-116 (1993).
Ahlneck et al., "The Molecular Basis of Moisture Effects on the Physical and Chemical Stability of Drugs in the Solid State", Int's J. Pharm. 62: 87-95 (1990).
Akers, M. J. et al., "Glycine Crystallization During Freezing: The Effects of Salt Form, pH, and Ionic Strength", *Pharmaceutical Research* 12(10):1457-1461 (1995).
Akoh et al., "One-stage synthesis of raffinose fatty acid polyesters", *J. Food Sci.* 52:1570-1576 (1987).
Alberts, B. et al., *Molecular Biology of the Cell*, 2nd ed., Garland Publishing, Inc., Ch. 2, p. 58, (1989).
Aldous et al., "The Crystallization of Hydrates from Amorphous Carbohydrates", *Cryo-Letters* 16:181-186 (1995).
Allison, S. D. et al., "Mechanisms of Protection of Cationic Lipid-DNA Complexes During Lyophilization", *Journal of Pharmaceutical Sciences* 89(5): 682-691 (2000).
Allison, S. D. & Anchordoquy, Thomas J., *Lyophilization of Nonviral Gene Delivery Systems*, Methods in Molecular Medicine, Nonviral Vectors for Gene Therapy, Ch. 18, 225-252 (Mark A. Findeis ed., Humana Press, 2001).
Anekwe, J. et al., "Relaxation Constants as a Predictor of Protein Stabilization," *Biocalorimetry: Applications of Calorimetry in the Biological Science*, J. E. Ladbury and B. Z. Chowdhry, editors, John Wiley & Sons, pp. 243-251 (1998).
Anchordoquy, Thomas J. et al., Physical Stabilization of DNA Based Therapeutics, 6(9) DDT 463-470 (May 2001).
"Drug Absorption and Availability", Modern Pharmaceutics, 3rd edition, G. S. Banker et al. (eds), Marcel Dekker, Inc., p. 145 (1996).
Barnett, A. H. "Exhubera Inhaled Insulin: A Review", *Int. J. Clin. Pract.* 58(4): 394-401 (2004).
Belopol'skaya, T. V. et al., The Effect of Water as Natural Plasticizer on Thermal Properties of Denaturated DNA Studied by Calorimetry 4 Vestnik Sankt-Petersburgskogo Universiteta Seriya pp. 16-22, abstract only, 2 pgs. (1999).
Bigsbee et al., "Solid State Liability of Insulin: Comparison of Crystalline and Amorphous Forms," *Pharmaceutical Research* 10(10): Abstract No. PDD 7418, p. S-279 (1993).
Blakely et al., "Dry instant blood typing plate for bedside use," *Lancet*, 336: 854-855 (1990).
Bögelein, J. et al., "Influence of Amorphous Mannitol on Powder Properties of Spray Dried Trehalose/Dextran Mixtures", [on-line] [retrieved Sep. 2005 ] Retrieved from the Internet <URL: http://www.pharmtech.unierlangen.de/APV_03_abs/bogelein.pdf> 2 pages (2003).
Bootsman, H.P.R. et al., "β-Cyclodextrin as an Excipient in Solid Oral Dosage Forms: In Vitro and In Vivo Evaluation of Spray-Dried Diazepan-β-Cyclodextrin Products," *International Journal of Pharmaceutics* 51:213-223 (1989).
Bosquillon, C. et al., "Aerosolization Properties, Surface Composition and Physical State of Spray-Dried Protein Powders", *Journal of Controlled Release* 99:357-367 (2004).
Branca, C. et al., "Destructuring effect of trehalose on the tetrahedral network of water: a Raman and neutron diffraction comparison", Physica A 304:314-318 (2002).
Branchu, S. et al. "The Effect of Cyclodextrins on Monomeric Protein Unfolding", *Biocalorimetry: Applications of Calorimetry in the Biological Science*, J. E. Ladbury and B.Z. Chowdhry (eds.), John Wiley & Sons, Ltd., 297-301 (1998).
Branchu, S. et al., "Hydroxypropyl-β-Cyclodextrin Inhibits Spray-Drying-Induced Inactivation of (β-Galactosidase", *Journal of Pharmaceutical Sciences* 88(9): 905-911 (1999).
Brange et al., "Chemical Stability of Insulin. I. Hydrolytic Degradation During Storage of Pharmaceutical Preparations," *Pharmaceutical Research* 9(6): 715-726 (1992).
Breitenbach, J. "Melt Extrusion: From Process to Drug Delivery Technology", *European Journal of Pharmaceutics and Biopharmaceutics* 54:107-117 (2002).
Brown, "A Therapeutic Panorama of the Spongiform Encephalopathies", *Antiviral Chem. Chemother.* 1(2): 75-83 (1990).
Buitink, Julia et al., *High Critical Temperature above Tg May Contribute to the Stability of Biological Systems* 79 Biophysical Journal 1119-1128 (Aug. 2000).
Burvall et al., "Storage of Lactose-Hydrolised Dried Milk: Effect of Water Activity on the Protein Nutritional Value", *Journal of Dairy Research* 45: 381-389 (1978).
Byron, Peter R. et al., *Drug Carrier Selection—Important Physicochemical Characteristics* Respiratory Drug Delivery, 5th Edition, Interpharm Press, 103-113 (1996).
Byström et al., "Microcalorimetry—A Novel Technique for Characterization of Powders", *Respiratory Drug Delivery IV*, 297-302 (1994).
Carpenter, John F. et al., "Rational Design of Stable Lyophilized Protein Formulations: Some Practical Advice", *Pharmaceutical Res.* 14:8:969-975 (1997).
Casselyn, M. et al., *Time-Resolved Scattering Investigations of Brome Mosaic Virus Microcrystals Appearance* D58 ACTH CRYST. 1568-1570 (2002).
Caughey et al., "Sulphated Polyanion Inhibition of Scrapie-Associated PrP Accumulation in Cultured Cells", *J. Virol.* 67(2): 643-650 (1993).
Chan et al., "Formulation of Vaccine Ajuvant Muramyldipeptides (MDP). 1. Characterization of Amorphous and Crystalline Forms of a Muramyldipeptide Analogue", *Pharmaceutical Research* 5(8): 523-527 (1988).
Chan, Hak-Kim et al, "Solid State Characterization of Spray-Dried Powders of Recombinant Human Deoxyribonuclease (RhDNase)", *Journal of Pharmaceutical Sciences*, 87(5):647-654 (1998).
Chan, Hak-Kim et al., "Physical Stability of Salmon Calcitonin Spray-Dried Powders for Inhalation" *Journal of Pharmaceutical Sciences* 93(3): 792-804 (2004).
Chavan, V. et al., "Effect of Rise in Simulated Inspiratory Flow Rate and Carrier Particle Size on Powder Emptying From Dry Powder Inhalers", *AAPS Pharmsci 2000*; 2(2) article 10 [on-line] Retrieved from the Internet < URL: http://www.pharmsci.org > 7 pages (2000).
Chavan, V. et al., "Novel System to Investigate the Effects of Inhaled Volume and Rates of Rise in Simulated Inspiratory Air Flow on Fine Particle Output From a Dry Powder Inhaler", *AAPS Pharmasci 2002*; 4(2) article 6 [on-line] Retrieved form the Internet < URL: http://www.aapspharmsci.org > 6 pages (2002).
Chavan, V. S. et al., "Effect of Particle Size and Rise in SImulated Inspiratory Flow Rate on Device Emptying in a Dry Powder Inhaler System", [on-line] [retrieved Jan. 7, 2005] Retrieved from the Internet <URL: htpp://www.aapspharmsci.org/abstracts/AM_1999/1001.htm > 1 page (1999).

Chawla et al, "Production of Spray Dried Salbutamol Sulphate for Use in Dry Powder Aerosol Formulation", *International Journal of Pharmaceutics* 108: 233-240 (1994).

Chiou et al., "Pharmaceutical Applications of Solid Dispersion Systems", *J. Pharm.* 60(9): 1281-1302 (1971).

Cleland et al, "The Development of Stable Protein Formulations: A Close Look at Protein Aggregation, Deamidation and Oxidation", *Critical Reviews in Therapeutic Drug Carrier Systems* 10(4): 307-377 (1993).

Cline, D. et al., "Predicting the Quality of Powders for Inhalation From Surface Energy and Area", *Pharmaceutical Research* 19(9):1274-1277 (2002).

Cline, D. et al., "Predicting the Quality of Powders for Inhalation", *Respiratory Drug Delivery VIII* 683-685 (2002).

Colaco et al., "Trehalose Stabilization of Biological Molecules", *Biotechnol. Internat.*, pp. 345, 347-350 (1992).

Colaco et al., "Chapter 14: Chemistry of Protein Stabilization by Trehalose", *ACS Symposium Series 567, Formulation and Delivery of Proteins and Peptides*, J.L. Cleland & R. Langer, pp. 222-240 (1994).

Costantino et al., "Moisture-Induced Aggregation of Lyophilized Insulin", *Pharmaceutical Research* 11(1): 21-29 (1994).

Costantino, H. R. et al., "Effect of Mannitol Crystallization on the Stability and Aerosol Performance of a Spray-Dried Pharmaceutical Protein, Recombinant Humanized Anti-IgE Monoclonal Antibody", *Journal of Pharmaceutical Sciences* 87(11):1406-1411 (1998).

Craig, I. D. et al., "Maillard Reaction Kinetics in Model Preservation Sytems in the Vicinity of the Glass Transition: Experiment and Theory", *J. Agric. Food Chem.* 49(10):4706-4712 (2001).

Crowe et al., "Interactions of Sugars with Membranes", *Biochimica et Biophysica Acta* 947: 367-384 (1988).

Crowe et al., "Are Freezing and Dehydration Similar Stress Vectors? A Comparison of Modes of Interaction of Stabilizing Solutes with Biomolecules", *Cryobiology*. 27:219-231.

Crowe, John H. et al., "The Role of Vitrification In Anhydrobiosis," *Annu. Rev. Physiol.* 60:73-103 (1998).

Crowe, Lois M. et al. "Is Trehalose Special for Preserving Dry Biomaterials?" *Biophysical Journal* 71:2087-2093 (1996).

D'Cruz, N. "Relationship Between Protein Thermal Stability and Glass Transition in Gelatin Polyol and Gelatin-Water Mixtures", Proceedings of 2004 Meeting IFT, Jul. 12-16, 2004, Las Vegas, NV, Session 17E, Food Chemistry: Proteins, [on-line] [retrieved Nov. 8, 2004] Retrieved from the Internet <URL: http://ift.confex.com/ift/2004/techprogram/paper_23006.htm > 17E-4 (2004).

Daemen et al., "The Destruction of Enzymes and Bacteria During the Spray-Drying of Milk and Whey, 2. The Effect of the Drying Conditions", *Neth. Milk Dairy J.* 36: 211-229 (1982).

Dalby, R. N. et al., "Inhalation Therapy: Technological Milestones in Asthma Treatment", *Advanced Drug Delivery* 55: 779-791 (2003).

Dalby et al., "Relationship Between Particles Morphology and Drug Release Properties After Hydration of Aerosols Properties Containing Liposome Forming Ingredients", *Pharmaceutical Research* 5(10): S-94, Abstract PD 888 (1988).

Darrington et al., "Evidence for a Common Intermediate in Insulin Deamidation and Covalent Dimer Formation: Effects of pH and Aniline Trapping in Dilute Acidic Solutions", *Journal of Pharmaceutical Sciences* 84(3): 275-282 (1995).

De Carlo, S. et al., "Unexpected Property of Trehalose as Observed by Cryo-Electron Microscopy", *Journal of Microscopy* 196(1):40-45 (1999).

Edwards, A. D. et al. "Crystallization of Pure Anhydrous Polymorphs of Carbamazepine by Solution Enhanced Dispersion With Supercritical Fluids (SEDS™)", *Journal of Pharmaceutical Sciences* 90(8): 1115-1124 (2001).

Eleutherio et al., "Role of the Trehalose Carrier in Dehydration Resistance of *Saccharomyces cerevisiae*," *Biochimica et Biophysica Acta* 1156: 263-266 (1993).

Elkordy et al., "Integrity of crystalline lysozyme exceeds that of a sapray-dried form", *International Journal of Pharmaceutics* 247:79-90 (2002).

Fahy et al., "Vitrification as an Approach to Cryopreservation", *Cryobiology* 21: 407-426 (1984).

Fakes, M. G. et al., "Moisture Sorption Behavior of Selected Bulking Agents Used in Lyophilized Products", *PDA J. Pharm Sci. Technol.* 54(2): 144-149, Abstract only [on-line] [retrieved Sep. 25, 2005] Retrieved from the Internet < URL: http://www.ncbi.nlm.nih.gov. > (2000).

Finar, I. L. "§14. Trehalose, m.p. 203°C.," under "Carbohydrate," *Organic Chemistry*, vol. 2, *Stereochemistry and the Chemistry of Natural Products*, 5th edition, Longman, p. 323 (1996 ).

Forbes, R. T. et al., "Water Vapor Sorption Studies on the Physical Stability of a Series of Spray-Dried Protein/Sugar Powders for Inhalation", *Journal of Pharmaceutical Sciences* 87(11): 1316-1321 (1998).

Franks, "Separation, Improved Freeze-Drying, an Analysis of the Basic Scientific Principles", *Process Biochemistry* 24(1): iii-vii (1989).

Franks, "Accelerated Stability Testing of Bioproducts: Attractions and Pitfalls", *TIBTECH* 12:114-117 (1994).

Fukuoka et al., "Glassy State of Pharmaceuticals. V.Relaxation During Cooling and Heating of Glass by Differential Scanning Calorimetry", *Chem. Pharm. Bull.* 39(8): 2087-2090 (Aug. 2001).

Green et al., "The Protein-Glass Analogy: Some Insights from Homopeptide Comparisons", *J. Phys. Chem.* 98:13780-13790 (Apr. 1994).

Green et al., "Phase Relations and Vitrification in Saccharide-Water Solutions and the Trehalose Anomaly", *J. Phys. Chem.* 93:2880-2882 (1989).

Gupta, A. et al., "Single Virus Particle Mass Detection Using Microresonators with Nanoscale Thickness", *Applied Physics Letters* 84(11):1976-1978 (2004).

Hahn et al, "Solid Surfactant Solutions of Active Ingredients in Sugar Esters", *Pharmaceutical Research* 6: 958-959 (1989).

Hancock et al., "The Use of Solution Theories for Predicting Water Vapor Absorption by Amorphous Pharmaceutical Solids; A Test of the Flory-Huggins and Vrentas Models", *Pharmaceutical Research* 10(9): 1262-1267 (1993).

Hancock et al., "Molecular Mobility of Amorphous Pharmaceutical Solids Below Their Glass Transition Temperatures", *Pharmaceutical Research* 12(6): 799-806 (1995).

Hancock, B. C. et al., "The Effect of Temperature on Water Vapor Sorption by Some Amorphous Pharmaceutical Sugars", *Pharmaceutical Development and Technology* 4(1): 125-131 (1999).

Hancock, B. C. et al., "Characteristics and Significance of the Amorphous State in Pharmaceutical Systems", *J. of Pharmaceutical Sciences* 86(1):1-12 (1997).

Hancock et al., "A Pragmatic Test of Simple Calorimetric Method for Determining the Fragility of Some Amorphous Pharmaceutical Materials", *Pharm Res.* 15(5): 762-767 (1998).

Hanes et al., "Porous Dry-Powder PLGA Microspheres coated with Lung Surfactant for Systemic Insulin Delivery Via the Lung", *Proc. Int;l Symp. Control Rel. Bioactive Matter* 24:57-58 (1997).

Hatley, R. H. M. et al., "Stabilization of Labile Materials by Amorphous Carbohydrates Glass Fragility and the Physiochemical Properties that Make Trehalose a Superior Excipient", *Pharmaceutical Research* 13(9 Suppl.) PDD 7165: S274 (1996).

"Pfizer and Inhale Therapeutic Systems Enter Pulmonary Insulin Collaboration for Dry Powder Aerosol Delivery", *Health News Daily* 7(13):4-5 (1995).

Heitefuss et al., "The Stabilization of Extracts of Cabbage Leaf Proteins by Polyhydroxy Compounds for Electrophoretic and Immunological Studies", *Archives of Biochemistry and Biophysics* 85:200-2008 (1959).

Heller, Martin C. et al., *Protein Formulation and Lyophilization Cycle Design: Prevention of Damage Due to Freeze-Concentration Induced Phase Separation* 63 Biotechnology & Bioengineering 166-174 (1999).

Herrington, T. M. et al., "Physico-Chemical Studies on Sugar Glasses. I. Rates of Crystallization," *Journal of Food Technology* 19:409-425 (1984).

Hickey, A. J. et al., "Behavior of Hygroscopic Pharmaceutical Aerosols and the Influence of Hydrophobic Additives," *Pharmaceutical Research* 10(1):1-7 (1993).

Hoener, Betty-Ann et al., "Factors Influencing Drug Absorption and Availability", *Modern Pharmaceutics*, Gilbert S. Banker et al., eds., Marcel Dekker Inc., Chapter 4, pp. 121-153 (1996).

Ibrahim, A. L. et al., "Spray Vaccination With an Improved F Newcastle Disease Vaccine. A Comparison of Efficacy With the B1 and La Sota Vaccines," *Br. Vet. J.* 139:213-219 (1983).

Iglesias et al., "Absorption Isotherm of Amorphous Trehalose", *J. Sci. food Agric.* 75:183-186 (1997).

Jameel, F. et al., "Freeze Drying Properties of Some Oligonucleotides", *Pharmaceutical Development and Technology* 6(2):151-157 (2001).

Jovanovic-Peterson, L. et al "Jet-injected insulin is associated with decreased antibody production and postprandial glucose variability when compared with needle-injected insulin in gestational diabetic women," *Diabetes Care* 16(11):1479-1484 (Nov. 1993).

Kachura, "Method of Drying Lactic Acid Bacteria," Vinodelie I Vinogradarstvo SSSR 2:49-50, English Abtract only, one page (1985).

Kanna, K. et al. "Denaturation of Fish Muscle Protein by Dehydration" *Bull. Tokai Reg. Fish. Res. Lab.* 77:70-76 English abstract (1974).

Karmas, R. et al., "Effect of Glass Transition on Rates of Nonenzymatic Browning in Food Systems," *J. Agric. Food Chem.* 40:873-879 (1992).

Khan, R. (1984). "Chemistry And New Uses Of Sucrose: How Important?" *Pure & Appl. Chem.* 56(7):833-844.

Khan et al., "Cyclic Acetals of 4,1',6'-Trichloro-4,1'6'-Trideoxy-Galacto-Sucrose and Their Conversion into Methyl Ether Derivatives", *Carb. Res.* 198:275-283 (1990).

Klein, T. M. et al., "High Velocity Microprojectiles For Delivering Nucleic Acids Into Living Cells," *Nature* 327:70-73 (1987).

Labuza et al., "Glass Transition Temperatures of Food Systems", [on-line] [retrieved Sep. 2005] Retrieved from the Internet <URL: http://faculty.che.umn.edu/fscn/Ted_Lebuza/PDF_files/Isotherm_Folder/Tg%20compilation.pdf > pp. 1-31 (Jan. 1992).

Lai, M. C. et al., "Solid-State Chemical Stability of Proteins and Peptides", *Journal of Pharmaceutical Sciences* 88(5):489-500 (1999).

Laube, B. L. et al., "Targeting Aerosol Deposition in Patients With Cystic Fibrosis, Effects of Alterations in Particle Size and Inspiratory Flow Rate", *Chest* 118(4): 1069-1076 (2000).

Ledl, F., et al., "New Aspects of the Maillard Reaction in Foods and in the Human Body," *Ang. Chem, Int. Ed.* Engl. 29:565-594 (Jun. 1990).

Lee, C. K. *Developments in Food Carbohydrate* —2nd edition Applied Science Publishers, London, Table of Contents, 4 pages (1980).

Lee, G., "Spray Drying of Proteins," Chapter 6, *Rational Design of Stable Protein Formulations, Theory and Practice*, J. F. Carpenter & M. Manning, pp. 135-158 (2002).

Lehninger, Albert L. *DNA and the Structure of the Genetic Material*, BIOCHEMISTRY, Chapter 31, 859-890 (Worth Publishers Inc., 2nd edition, 1975).

Leslie, S. B. et al., "Trehalose and sucrose protect both membranes and proteins in intact bacteria during drying", *Appl. Env. Microbiol.* 61(10): 3592-3597 (1995).

Leuner, C. et al. "Improving Drug Solubility for Oral Delivery Using Solid Dispersions", *European Journal of Pharmaceutics and Biopharmaceutics* 50:47-60 (2000).

Li, Z. et al., "Realistic In Vitro Assessment of Dry Powder Inhalers", *Respiratory Drug Delivery VIII*, pp. 687-689 (2002).

Lin, S.-Y. et al., "Solid Particles of Drug-β-Cyclodextrin Inclusion Complexes Directly Prepared by a Spray-Drying Technique", *International Journal of Pharmaceutics*, 56:249-259 (1989).

Liu, Jinsong et al., "Dynamics of Pharmaceutical Amorphous Solids: The Study of Enthalpy Relaxation by Isothermal Microcalorimetry", *Journal of Pharmaceutical Sciences* 91(8):1853-1862 (2002).

Louey, M. D. et al., "Controlled Release Products for Respiratory Delivery", *APR*, 7(4):82-87 [on-line] [retrieved Sep. 2005] Retrieved from the Internet < URL: http://www.americanpharmaceuticalreview.com/article.aspx?article=77 > 11 pages (2004).

Louis, P. et al., "Survival Of *Escherichia coli* during Drying And Storage In The Presence of Compatible Solutes" *Appl. Microbiol. Biotechnol.* 41:684-688 (1994).

Lueckel, B. et al., "Effects of Formulation and Process Variables on the Aggregation of Freeze-Dried Interleukin-6 (IL-6) After Lyophilization and on Storage", *Pharmaceutical Development and Technology* 3(3):337-346 (1998).

Martin, A. et al., *States of Matter and Phase Equilibria* Physical Pharmacy, Physical Chemical Principles in the Pharmaceutical Sciences, 3rd. ed., Chapter 4, 62-92 (1983).

Matsuda, Y. et al., "Amorphism and Physicochemical Stability of Spray Dried Frusemide," *J. Pharm. Pharmacol.* 44:627-633, received Nov. 7, 1991 (1992).

Masters, K. Spray Drying Handbook, England; Longman Scientific & Technical and John Wiley & Sons, Inc., 5th ed., pp. 309-352 (1991).

Masters, K. Spray Drying Handbook, England; Longman Scientific & Technical, 5th ed., pp. 640-642 (1991).

Mattern et al., "Formulation of Proteins in Vacuum-Dried Glasses. II. Process and Storage Stability in Sugar-Free Amino Acid Systems", Pharmaceutical Development &Technology 4(2):199-208 (1999).

Miller, D. P. et al., "Stabilization of Lactate Dehydrogenase Following Freeze-Thawing and Vacuum-Drying in the Presence of Trehalose and Borate", *Pharmaceutical Research* 15(8):1215-1221 (1998).

Molina, M. C. et al., "The Stability of Lyophilized Lipid/DNA Complexes During Prolonged Storage," *J. Pharm. Sci.* 93(9):2259-2273, abstract only, one page, [on-line] [retrieved Sep. 2005] Retrieved from the Internet <URL: http://www.ncbi.nlm.nih.gov>, (2004).

Mouradian, R. et al., "Degradation of Functional Integrity During Long-Term Storage of a Freeze-Dried Biological Membrane", *Cryobiology* 22: 119-127 (1985).

Moynihan et al., "Dependence of the Glass Transition Temperature on Heating and Cooling Rate", *J. Physical. Chem.* 78(26): 2673-2677 (1974).

Murphy, B. R. et al., "Chapter 19: Immunization Against Viruses", in *FieldsVirology*, 2$^{nd}$ Edition, vol. 1, Raven Press, pp. 469-502 (1990).

Murphy, Brian R. et al., *Fields Virology*, vol. 1, Chapter 16, *Immunization Against Virus Disease*, 467, at p. 468, first full paragraph, first column, lines 26-33 (Bernard N. Fields et al. eds., Lippincott-Raven Publishers, 3rd ed. 1996).

Nabel, G. J. et al., "Immunotherapy of Malignancy by In Vivo Gene Transfer Into Tumors," *Hum. Gene. Ther.* 3(4): 399-410 (Aug. 1992) Abstract only [on-line] [retrieved 112/21/04] Retrieved from the Internet < URL: http://www.ncbi.nlm.nih.gov/entrez/query.fcgi?cmd=Retrieve&db=pubmed&dopt=Abstr >.

Naini, V. et al., "Particles for Inhalation Produced by Spray Drying and Electrostatic Precipitation of Different Protein-Sugar Solutions", *Respiratory Drug Delivery V*, pp. 382-384 (1996).

Naini, V. et al., "Physicochemical Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Natarajan, P., Crystallization Conditions for VIPER Entries [on-line] [retrieved Nov. 4, 2004] Retrieved from the Internet <URL: http://www.xtal.tsinghua.edu.cn/research/groups/web/material/Virus%20Crystallization%20Page.htm > pages (last updated Jan. 3, 2002).

Niven, R. W. "Delivery of Biotherapeutics by Inhalation Aerosol," *Critical Reviews in Therapeutic Drug Carrier Systems*, 12(2&3):151-231 (1995).

Niven, R. W. "Delivery of Biotherapeutics by Inhalation Aerosols," *Pharmaceutical Technology* 72-75, 80 (Jul. 1993).

Norberg, J. et al., "Glass Transition in DNA From Molecular Dynamics Simulation", *Proc. Natl. Acad. Sci. USA* 93:10173-10176 (1996).

Odegard, P. S. et al., "Inhaled Insulin: Exubera", *The Annals of Pharmacotherapy* 39:843-853 (2005).

Ohtake, S. et al., "Effect of pH, Counter Ion and Phosphate Concentration on the Glass Transition Temperature of Freeze-Dried Sugar-Phosphate Mixtures", *Pharmaceutica Research* 21(9):1615-1621 (2004).

Okamoto, H. et al., "Dry Powders for Pulmonary Delivery of Peptides and Proteins", *Kona* 20:71-83 (2002).

Oksanen et al., "The Relationship between the Glass Transition Temperature and Water Vapor Absorption by Poly(Vinylpyrrolidone)," *Pharmaceutical Research* 7(6): 654-657 and errata on p. 974 (1990).

Okumura, K. et al., "Intratracheal Delivery of Calcitonin Dry Powder in Rats and Human Volunteers," *S.T.P. Pharmaceutical Sciences* 4(1):5 pages (Jan., Feb. 1994).

Onodera et al., "Glass Transition of Dehydrated Amorphous Solid", *Bull. Chem. Soc. Japan* 41(9): 2222 (1968).

Owens, D. R. et al., "Alternative Routes of Insulin Delivery," *Diabetic Medicine* 20:886-898 (2003).

Palmer, K. J. et al. "X-Ray Diffractometer and Microscopic Investigation of Crystallization of Amorphous Sucrose," Agricultural and Food Chemistry 4(1): 77-81 (Jan. 1956).

Parks, "Studies on Glass. II The Transition Between the Glassy and Liquid States in the Case of Glucose", *Journal of Physical Chemistry* 1366-1379 (1928).

Patel, M. M. et al., "Degradation Kinetics of High Molecular Weight Poly(L Lactide) Microspheres and Release Mechanism of Lipid: DNA Complexes", *Journal of Pharmaceutical Sciences*, 93(10): 2573-2584 (2004).

Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).

Phillips, E. et al., "Size Reduction of Peptides and Proteins by Jet-Milling", *Respiratory Drug Delivery VI*, pp. 161-167 (1998).

Pikal, M. J. et al., "The Stability of Insulin in Crystalline and Amorphous Solids: Observation of Greater Stability for the Amorphous Form", *Pharmaceutical Research* 14(10):1379-1387 (1997).

Pikal et al., "Thermal Decomposition of Amorphous β-Lactam Antibacterials", *Journal of Pharmaceutical Science* 66(9): 1312-1316 (Sep. 1977).

Pikal, M. J. et al., Errata of"The Stability of Insulin in Crystalline and Amorphous Solids: Observation of Greater Stability for the Amorphous Form,"*Pharmaceutical Research* 15(2):362-363 (1998).

Pine, S. H. et al., "15-3 Oligosaccharides and Polysaccharides," *Organic Chemistry*, 4a' edition, McGraw-Hill International Book Company, p. 763 (1980).

Pisecky, J. "2. Evaporation and Membrane Filtration", *Handbook of Milk Powder Manufacture*, Niro A/S, Denmark, p. 3 (1997).

Pocchiari, M. et al. "Amphotericin B: A Novel Class of Antiscrapie Drugs," *J. Infect. Dis.* 160(5):795-802 (Nov. 1989).

Prestrelski, S. J. et al., "Optimization of Lyophilization Conditions for Recombinant Human Interleukin-2 by Dried-State Conformational Analysis Using Fourier-Transform Infrared Spectroscopy," *Pharmaceutical Research* 12(9):1250-1259 (1995).

Prestrelski, S. J. et al., "Separation of Freezing- and Drying-Induced Denaturation of Lyophilized Proteins Using Stress-Specific Stabilization," *Archives of Biochemistry and Biophysics* 303(2):465-473 (Jun. 1993).

Quan, C. *Protein Science* 4(2):148, Abstract No. 490-T (1995).

Ramanujam, R. et al., "Ambient-Temperature-Stable Molecular Biology Reagents," *Biotechniques* 14(3):470-473 (1993).

Ringe, D. et al., "The Glass Transition in Protein Dynamics: What it is, Why it Occurs, and How to Exploit It", *Biophys. Chem.* 105(2-3):667-680, Abstract only, [on-line] [retrieved Nov. 19, 2004] Retrieved form the Internet < URL: http://www.ncbi.nlm.nih.gov > (2003).

Roser et al. "A Sweeter Way To Fresher Food" *New Scientist* pp. 25-28 (May 15, 1993).

Roser, B. "Trehalose, A New Approach To Premium Dried Foods", *Trends in Food Sci. and Tech.* pp. 166-169 (Jul. 1991).

Roser, "Trehalose Drying: A Novel Replacement of Freeze Drying", *Biopharm*, 4:47-53 (1991).

Saleki-Gerhardt, A. et al., "Non-Isothermal and Isothermal Crystallization of Sucrose From the Amorphous State," *Pharmaceutical Research* 11(8):1166-1173 (1994).

Saleki-Gerhardt, A. et al., "Hydration and Dehydration of Crystalline and Amorphous Forms of Raffinose," *Journal of Pharmaceutical Sciences*, 84(3):318-323 (Mar. 1995).

Sambrook, et al., *Molecular Cloning: A Laboratory Manual*, 2nd. ed., "Concentrating Nucleic Acids: Precipitation with Ethynol or Isopropanol", pp. E.10-E.17, Cold Spring Harbor Laboratory Press (1989).

Sanchez, J. et al., "Recombinant System for Overexpression of Cholera Toxin B Subunit In Vibrio Cholerae as a Basis for Vaccine Development" *Proc. Natl. Acad. Sci.* USA 86:481-485 (1989).

Schamblin and Zografi, "Enthalpy Relaxation in Binary Amorphous Mixtures Containing Sucrose", *Pharmaceutical Research* 15(12): 1828-1834 (Dec. 1998).

Schebor, C. et al., "Color Formation Due to Non-Enzymatic Browning in Amorphous, Glassy, Anhydrous, Model Systems", *Food Chemistry* 65:427-432 (1999).

Sciarra et al., "Aerosols", *Remington's Pharmaceutical Sciences*, Chap. 93, 17th Ed., Mack Publishing Company, Alfonso R. Gennaro, editor, pp. 1662-1677 (1985).

Sebhatu, R. et al., "Assessment of the Degree of Disorder in Crystalline Solids by Isothermal Microcalorimetry," *International Journal of Pharmaceutics* 104:135-144 (1994).

Sellers, S. P. et al., "Dry Powders of Stable Protein Formulations From Aqueous Solutions Prepared Using Supercritical C02-Assisted Aerosolization", *Journal of Pharmaceutical Sciences* 90(6):785-797 (2001).

Serajuddin, A. T. M. et al., "Effect of Thermal History on the Glassy State of Indapamide," *J. Pharm. Pharmacol.* 38:219-220 (1986).

Shalaev et al., "Structural Glass Transitions and Thermophysical Processes in Amorphous Carbohydrates and Their Supersaturated Solutions", *J. Chem. Soc. Farady Trans.* 91(10): 1511-1517 (1995).

Shalaev, E. Y. et al., "How Does Residual Water Affect The Solid-State Degradation of Drugs in the Amorphous State", *Journal of Pharmaceutical Sciences*, 85(11):1137-1141 (1996).

Sharma, V. K. et al., "Effect of Vaccum Drying on Protein-Mannitol Interactions: The Physical State of Mannitol and Protein Structure in the Dried State," *AAPS PharmSciTech* 5(1) Article 10:1-12 [on-line] Retrieved from the Internet <URL: http://www.aapspharmscitech.org > (2004).

Skrabanja et la., "Lyophilization of Biotechnology Products", *PDA J. Pharm. Sci. Technol.* 48(6):311-317 (1994).

Singer et a. l"Thermotolerance in *Saccharomyces cerevisiae*: the Yin and Yang of Trehalose", *Tibtech* 16:460-468 (1998).

Sokolov et al., "Glassy Dynamics in DNA: Ruled by Water of Hydration" *Journa of Chemical Physics* 110(14):7053-7057 (1999).

Sola-Penna et al., "Stabilization Against Thermal Inactivation Promoted by Sugars on Enzyme Structure and function: Why is Trehalose More Effective than Other Sugars", *Archives of Biochemistry and Biophysics* 360(1), Article No. BB980906:10-14 (1998).

Sonner, C. et al., "Spray-Freeze-Drying for Protein Powder Preparation: Particle Characterization and a Case Study With Trypsinogen Stability", *Journal of Pharmaceutical Sciences* 91(10):2122-2139 (2002).

Spi Polyols™ "What are Polyols? What do Polyols do? What are Polyols' functionality?", [on-line] [retrieved Jun. 25, 2004] Retrieved from the Internet <URL: http://www.spipolyols.com/whatarepolyols.html > one page (2003).

Strickley, R. G. et al., "Solid-State Stability of Human Insulin II. Effect of Water on Reactive Intermediate Partitioning in Lyophiles from pH 2-5 Solutions: Stabilization Against Covalent Dimer Formation", *Journal of Pharmaceutical Sciences* 86(6):645-653 (1997).

Strom, A. R. and Kaasen, I., "Trehalose Metabolism in *Escherichia coli*: Stress Protection and Stress Regulation of Gene Expression", *Molecular Microbiology* 8(2):205-210 (1993).

Stubberud, L. et al., "The Use of Gravimetry For The Study of the Effect of Additives on the Moisture-Induced Recrystallisation of Amorphous State", *International Journal of Pharmaceutics* 163:145-156 (1998).
Sukenik et al., "Enhancement of a Chemical Reaction Rate by Proper Orientation of Reacting Molecules in the Solid State", *J. Am. Chem. Soc*. 97: 5290-5291 (Sep. 1975).
Sussich, F. et al., "Reversible Dehydration of Trehalose and Anhydrobiosis: From Solution State to an Exotic Crystal?", *Carbohydrate Research* 334:165-176 (2001).

Takahashi et al., "Induction of CD8+ cytotoxic T cells by immunization with purified HIV-1 envelope protein in ISCOMs", *Nature* 344:873-875 (Apr. 1990).

Tarelli, E. et al., "Additives to Biological Substances. III. The Moisture Content and Moisture Uptake of Commonly Used Carrier Agents Undergoing Processing Conditions Similar to Those Used in the Preparation of International Biological Standards," *Journal of Biological Standardization* 15:331-340 (1987).

Thatcher, E., "Quantitation of Virus" [on-line] [retrieved Nov. 1, 2004] Retrieved from the Internet <URL: http://www.sonoma.edu/users/t/thatcher/bio1383/lab.htm > 4 pages, (last updated Jan. 5, 2002).
Timko et al. "Thermal Analysis Studies of Glass Dispersion Systems", *Drug Devel. Ind. Pharm*. 10:425-451 (1984).
Timsina, T. et al., "Drug Delivery to the Respiratory Tract Using Dry Powder Inhalers," *International Journal of Pharmaceutics* 101:1-13 (1994).
To et al., "Collapse, a Structural Transition in Freeze Dried Carbohydrates", *J. Fd. Technol*. 13: 567-581 (1978).
Tsourouflis et al., "Loss of Structure in Freeze-Dried Carbohydrates Solutions: Effect of Temperature, Moisture Content and Composition", *J. Sci. Food Agric*., vol. 27, pp. 509-519, 1976.
Ulrich, "Biophysical Aspects of Using Liposomes as Delivery Vehicles", *Bioscience Reports* 22(2):129-150 (2002).
Uritani, M. et al., "Protective Effect of Disaccharides on Restriction Endonucleases During Drying Under Vacuum," *J. Biochem*. 117:774-779 (1995).
Vain et al., "Development of the particle inflow gun", *Plant Cell, Tissue and Organ Culture* 33:237-246 (1993).

Vavelyuk, O.L. et al., "Thermostability of DNA and Its Association with Vitrification", *Tsitologiya* 41(11):958-965 (1999).

Vidgrén, M. T. et al., "Comparison of Physical and Inhalation Properties of Spray-Dried and Mechanically Micronized Disodium Cromoglycate," *International Journal of Pharmaceutics* 35:139-144 (1987).

Vromans, H. et al., "Studies on Tableting Properties of Lactose. VII. The Effect of Variations in Primary Particle Size and Percentage of Amorphous Lactose in Spray Dried Lactose Products," *International Journal of Pharmaceutics* 35:29-36 (1987).

Wang, et al. eds. *Stability and characterization of protein and peptide drugs*, Table of Contents, 6 pages (1993).

Welsh, D. T., "The Role of Compatible Solutes In the Adaptation and Survival of *Escherichia coli*," Ph.D. Thesis Submitted to Department of Biological Sciences, University of Dundee. pp. 1-262 . (Aug. 1992).

Williams et al., "The Temperature Dependence of Relaxation Mechanisms in Amorphous Polymers and Other Glass Forming Liquids", *The Journal of the American Chemical Society* 77: 3701-3707 (1955).
Williams et al., "The Glassy State in Corn Embryos", *Plant Physiol*., vol. 89, pp. 977-981, 1989.
Xi, Y. G. et al., "Amphotericin B Treatment Dissociates in Vivo Replication of the Scrapie Agent From PrP Acummulation", *Nature* 356:598-601 (Apr. 1992).
Yoshida et al., "Absorption of Insulin Delivered to Rabbit Trachea Using Aerosol Dosage Form", *Journal of Pharmaceutical Sciences* 68(5):670-671 (1979).
Yoshinari, T. et al., "Moisture Induced Polymorphic Transition of Mannitol and its Morphological Transformation", *International Journal of Pharmaceutics*, 247:69-77 (2002).
Yoshioka, M. et al., "Crystallisation of Indomethacin From the Amorphous State Below and Above Its Glass Transition Membrane," *Journal of Pharmaceutical Sciences* 83(12):1700-1705 (Dec. 1994).
Zubay, G. Biochemistry, Second Edition, pp. 39 & 169, Table 5-6 Major Steroid Hormones (1988).
Zubay, G. Biochemistry, Second Edition, pp. 216-232 "Structural Properties of DNA" (1988).
Nektar U.S. Appl. No. 08/044,358, "Compositions and Methods For Nucleic Acid Delivery To The Lung" filed by Patton et al. on Apr. 7, 1993, assigned to Inhale Therapeutic Systems.
Nektar U.S. Appl. No. 08/442,563, filed Apr. 14, 1995, Paper No. 17, Office Communication mailed Apr. 3, 1998 (Patent No. 5,994,314).
Ibrahim, A. L. et al., "Spray Vaccination With an Improved F Newcastle Disease Vaccine. A Comparison of Efficacy With the B1 and La Sota Vaccines," *Br. Vet. J.* 139:213-219 (1983).
Broadhead , J. et al., "The Spray Drying of Pharmaceuticals", *Drug Development and Industrial Pharmacy* 18(11 & 12): 1169-1206, 1992.
Levine and Slade, "Another View of Trehalose for Drying and Stabilizing Biological Materials", *BioPharm*., 36-40, 1992.
Broadhead, J. et al., "The Effect of Process and Formulation Variables on the Properties of Spray-dried β-Galactosidase", *J. Pharm. Pharmacol*. 46:458-467, 1994.
Mumenthaler et al., "Feasibility Study on Spray-Drying Protein Pharmaceuticals: Recombinant Human Growth Hormone and Tisseu-Type Plasminogen Activator", *Pharmac. Research* 11(1): 12-20, 1994.
Derwent English abstract for DD 161072, published Sep. 18, 1984, entitled "Microbial beta - 1,3-1,4-glucanase enzyme prodn. by submerged fermentation of rifamycin-resistant Bacillus amyloliquefaciens strain in presence of native starch".
English Translation of, Toyama, A. (ed) Handbook of Natural Product for food processing, 9th Edition, Osaka, Japan, Shokuhin to Kagaku Sha, pp. 384 and 495 (ISBN4-87994-048-8), (1986).
English Abstract of BE 902257, published on Aug. 8, 1985.
Partial English Translation of DE 1 080 265, published on Apr. 21, 1960.
English Abstract of DE 31 41 498 A1, published on Apr. 28, 1983.
English Abstract of ES 8403520, published on Jun. 16, 1984.
English Abstract of FR 2238476, published on Mar. 28, 1975.
English Abstract only of GB 2 187 191, published on Sep. 3, 1987.
English Abstract of JP 02-000111, published on Jan. 5, 1990.
English Abstract of JP 52-139789, published on Nov. 21, 1977.
English Abstract of JP 58-216695, published on Dec. 16, 1983.
English Abstract of JP 59-095885, published on Jun. 2, 1984.
English Abstract of JP 60-244288, published on Dec. 4, 1985.
English Abstract of JP 62-228272, published on Oct. 7, 1987.
English Abstract of JP 62-255434, published on Nov. 7, 1987.
English Abstract of JP 06-100464, published on Apr. 12, 1994.
English Abstract of WO 92/10515, published Jun. 25, 1992.

* cited by examiner

Serum profiles of PTH34 in rats following intravenous and intratracheal administration Human Parathyroid Hormone PTH 84 Pulmonary Absorption in Rats

SEQUENCE LISTING

```
<160> NUMBER OF SEQ ID NOS: 1
<210> SEQ ID NO 1
<211> LENGTH: 38
<212> TYPE: PRT
<213> ORGANISM: Artificial Sequence
<220> FEATURE:
<223> OTHER INFORMATION: parathyroid hormone (PTH) fragment molecues

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly
        35
```

PULMONARY DELIVERY OF ACTIVE FRAGMENTS OF PARATHYROID HORMONE

This application is a continuation of application Ser. No. 09/577,264, filed May 22, 2000, which application is a continuation of application Ser. No. 09/128,401, filed Aug. 3, 1998, now issued as U.S. Pat. No. 6,080,721, which application is a divisional of application Ser. No. 08/625,586, filed Mar. 28, 1996, now issued as U.S. Pat. No. 5,814,607, which application is a continuation of application Ser. No. 08/232,849, filed Apr. 25, 1994, now issued as U.S. Pat. No. 5,607,915, which application is a continuation of application Ser. No. 07/953,397, filed Sep. 29, 1992, now abandoned, the full disclosures of which are incorporated herein by reference.

BACKGROUND OF THE INVENTION

1. Field of the Invention

The present invention relates generally to methods and compositions for systemic administration of parathyroid hormone to mammalian hosts. More particularly, the present invention relates to pulmonary administration of active parathyroid hormone fragments to provide pulsatile serum concentration profiles.

Human parathyroid hormone (PTH) is an 84 amino acid protein that is involved in calcium and phosphorus homeostasis and control of bone growth and density. N-terminal fragments of PTH, particularly those consisting of amino acids 1-34 and 1-38, retain the full biological activity of the intact protein. Recently, the use of PTH and PTH fragments in combination with vitamin D or dietary calcium was found to be effective in the treatment of osteoporosis when administered to a host on a periodic, preferably daily, basis.

Heretofore, the administration of PTH and PTH fragments has generally been accomplished subcutaneously, i.e., through injection. The need to inject PTH (or any other drug) on a daily basis, however, is undesirable. Most patients have an aversion to self-injection of drugs, and the need to visit a clinic or doctor's office for administration is inconvenient and burdensome. While other forms of administration have been suggested, such as oral delivery to the stomach, transdermal delivery, and nasopharyngeal absorption, none of these delivery routes has been proven to be effective and each suffers from certain drawbacks. Oral delivery results in very low bioavailability of polypeptide drugs, usually below 1%, due to degradation in the gastrointestinal tract. Moreover, the epithelial lining of the gastrointestinal tract is impermeable to most polypeptides. Nasopharyngeal and transdermal delivery avoid the problems of enzyme degradation, but usually require penetration enhancers in order to effect systemic absorption. Even with such penetration enhancers, bioavailability will usually be very low, and the penetration enhancers can often cause undesirable irritation. In the case of nasopharyngeal administration, penetration enhancers can often damage the nasal epithelium and chronic use has been associated with hyperplasia of the nasal lining.

Pulmonary or respiratory delivery of polypeptide drugs has also been suggested. Relatively large proteins, such as growth factors and cytokines which are typically larger than 150 amino acids, are often readily absorbed through the cellular lining of the alveolar region of the mammalian lung. Advantageously, such absorption can be achieved without the use of penetration enhancers. The pulmonary absorption of smaller proteins, usually below 100 amino acids in length, is much less predictable. Many smaller native polypeptides are not absorbed by the mammalian lung, but certain examples such as insulin (51 amino acids) and calcitonin (32 amino acids) have been found to be systemically absorbed when delivered to the lung. Even when a protein drug is systemically absorbed by a host through the lung, the pharmacological kinetics of the drug are unpredictable. Thus, both the amount and timing of drug bioavailability are unpredictable.

It is presently believed that PTH is most effectively delivered to a patient in a pulsatile fashion. That is, serum concentrations of PTH should rise rapidly after administration and fall rapidly after a peak has been reached, generally resulting in a spike in the serum concentration profile. Thus, it is advantageous for any route of PTH delivery to provide such a serum concentration profile.

For these reasons, it would be desirable to provide alternative delivery methods for parathyroid hormone which are patient acceptable. Such methods should avoid subcutaneous injection, limit irritation to the skin and body mucosa, and provide a desired pulsatile delivery profile discussed above. Such methods should further provide for high levels of PTH bioavailability, be amenable to self-administration by the patient, and be economic.

2. Description of the Background Art

U.S. Pat. Nos. 4,333,125 and 4,698,328, describe the administration of active parathyroid hormone fragments in combination with vitamin D or a dietary calcium supplement. Suggested administration routes include parenteral by injection, rapid infusion, nasopharyngeal absorption, dermal absorption, or oral. See also, Neer et al. (1987) Osteoporosis 53:829-835. U.S. Pat. No. 5,011,678, describes the use of amphophilic steroids as a penetration enhancer for nasal or bronchopulmonary delivery of proteins and polypeptides, listing parathyroid hormone as one of a "veritable host" of proteins which could be delivered with the enhancer. Parathyroid hormone (full length) is secreted naturally from the carathyroid gland as a series of spikes in a pulsatile fashion which is analogous to pituitary hormones (Harms et al. (1987) Int. Symp. on Osteoporosis, Aalborg, Abstract 232). The full length hormone is rapidly broken down in the circulation to several fragments which are the dominant serum forms. It is hypothesized that an intermittent or pulsatile secretion pattern or parathyroid hormone is necessary to maintain its bone restoring properties (Hesch et al. (1988) Calcif. Tissue Int. 42:341-344 and Habener et al. (1971) Proc. Natl. Acad. Sci. USA 63:2986-2991). Patton and Platz (1992) Adv. Drug Deliver. Rev. 8:179-196. describe methods for delivering proteins and polypeptides by inhalation through the deep lung.

SUMMARY OF THE INVENTION

According to the present invention, methods and compositions for the systemic delivery of parathyroid hormone (PTH) to a mammalian host, particularly a human patient suffering from or at risk of osteoporosis, provide for a preferred pulsatile concentration profile of the PTH in the host's serum after administration. In particular, the methods of the present invention rely on pulmonary or respiratory delivery of a biologically active N-terminal fragment of PTH, where delivery of the fragment through the alveolar region of the lung results in a rapid concentration spike of PTH in the host serum followed by a quick decrease in concentration. Surprisingly, pulmonary delivery of intact PTH protein under the same conditions will result in a relatively constant serum concentration of PTH over an extended time period. The ability to obtain the desired pulsatile serum concentration profile by pulmonary delivery of the PTH fragments, in contrast to the delivery of intact PTH, could not have been predicted with any degree of certainty prior to the work reported herein.

According to an exemplary embodiment, the method of the present invention comprises dispersing a preselected amount of the PTH fragment in a volume of gas to produce an aerosolized bolus. The PTH fragment usually consists of the N-terminal 34 or 38 amino acids of the PTH molecule but may be an N-terminal fragment of any size which display the desired pharmacokinetic profile, usually being 50 or fewer amino acids), and the dispersion may be produced by introducing a dry powder of the fragment into a high velocity gas stream, by nebulizing a liquid solution or suspension of the fragment, or by releasing a propellant containing the PTH fragment through a nozzle. The patient then inhales the aerosolized bolus through the mouth and into the alveolar region of the lungs. By repeating the dispersing and inhaling steps a sufficient number of times, a desired total dosage of the PTH fragment can be delivered to the patient.

Pharmaceutical compositions according to the present invention include dry powder formulations where the PTH fragment is present as a powder having a mean particle size in the range from 0.5 μm to 5 μm in a pharmaceutically acceptable dry bulking powder, where the PTH is present at from 1% to 10%. A pharmaceutical composition suitable for nebulization comprises the biologically active fragment of PTH present in an aqueous buffer at pH 4-6 in a concentration in the range from 1 mg/ml to 20 mg/ml. Pharmaceutical compositions suitable or propellant dispersion comprise a powder of the PTH having a mean particle size in the range from 0.5 μm to 5 μm present in an aerosol propellant.

In addition to the preferred pulsatile pharmacokinetic serum profile of the PTH fragments, the methods and compositions of the present invention provide a high level of patient acceptability. PTH administration does not require injection and can be self-administered by the patient on a daily basis, usually without complications such as those associated with transdermal and intra nasal delivery. The methods and compositions of the present invention also provide for a high level bioavailability of the PTH, and are economic.

DESCRIPTION OF SPECIFIC EMBODIMENTS

Figure 1:
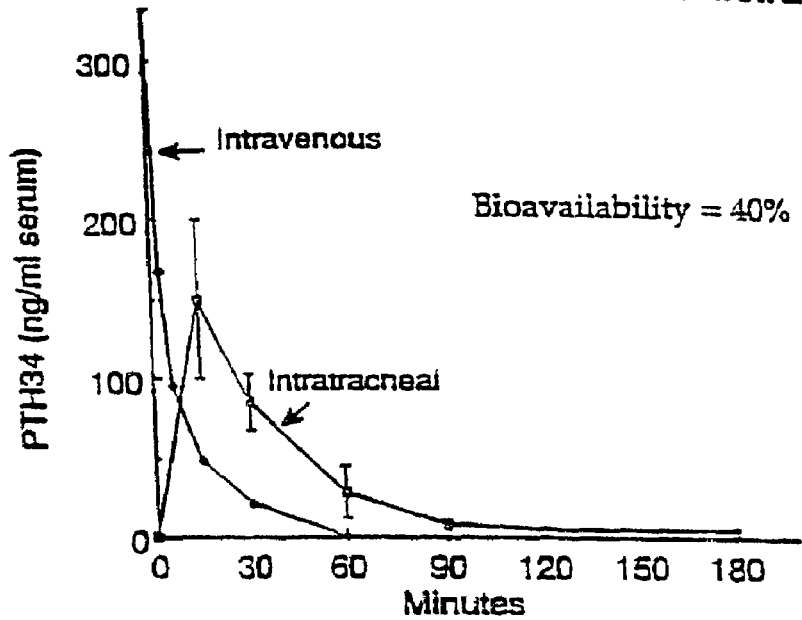
FIG. 1 is a graph illustrating the serum profile over time of PTH34 administered intravenously and intratracheally to rats, as described in detail in the Experimental section hereinafter.

Parathyroid hormone (PTH) is delivered to a mammalian host by inhalation into the alveolar region of the host's lungs. The cellular lining of the deep mammalian lung is extremely thin (0.1 μm) and has been found to be naturally permeable to both full length PTH and certain biologically active and N-terminal fragments of PTH, as described below. Surprisingly, however, such pulmonary or respiratory delivery of the PTH fragments only (and not the full length PTH) has been found to provide a desired pulsatile serum concentration profile of the PTH, as is believed to enhance the biological activity of the PTH, particularly when treating osteoporosis.

Thus, the present invention provides for the pulmonary or respiratory delivery of biologically active N-terminal fragments of PTH by inhalation by a patient through the mouth, where such fragments have a size which is less than that of full size native human PTH (human PTH is 84 amino acids) and which results in a pulsatile serum concentration profile characterized by a rapid rise to a peak and followed by a rapid fall. The PTH fragments will preferably be fragments of human PTH (or recombinantly produced polypeptides having the sequence of human PTH), typically including up to about 50 amino acids from the N-terminus of the PTH molecule, more preferably consisting of either amino acids 1-34 or amino acids 1-38 of human PTH, as set forth in Table 1 below.

Useful biologically active fragments of PTH also include chemically modified parathyroid hormone fragments which retain the activity associated with parathyroid hormone. The necessary activity is the stimulation of bone formation. Modifications that may be considered include:

(1) PTH fragments with carboxyl amino acid extensions beyond position 34 (but usually not beyond position 50) of the human PTH molecule, or aminoterminal extensions, or amino acid substitutions that produce other desirable features, such as an alpha-carboxyl amide at the carboxyl terminus. A desirable modification would enhance activity in vivo.

(2) PTH fragments extended to include amino acids 1-38, which would enhance receptor binding and hence the activity per mole.

(3) PTH fragments chemically modified so as to enhance through absorption through the alveolar region of the lung.

(4) Physiologically acceptable salts and esters of PTH fragments.

A PTH fragment obtainable from a mammal is generally preferred over other types of parathyroid hormone fragments, such as derivatives. Use of a PTH fragment consisting of the first thirty-four amino acid residues of human parathyroid hormone (hereafter abbreviated "PTH-34") is especially preferred for use in humans. Other preferred PTH fragments are those which display some or all of the following desirable features: increased potency with regard to the necessary activity, increased ease of administration, increased selectivity to decrease potential side effects, and decreased antigenicity in humans to avoid an adverse immune response. PTH fragments molecules having the sequences 1-34 or 1-38 of Table 1 are particular preferred:

TABLE 1

| 1 | | | | 5 | | | | |
|---|---|---|---|---|---|---|---|---|
| H$_2$N-Ser-Val-Ser-Glu-Ile-Gln-Leu-Met-His- |
| 10 | | | | 15 | | | | |
| Asn-Leu-Gly-Lys-His-Leu-Asn-Ser-Met-Glu- |
| 20 | | | | 25 | | | | |
| Arg-Val-Glu-Trp-Leu-Arg-Lys-Lys-Leu-Gln- |
| 30 | | | | 35 | | | | |
| Asp-Val-His-Asn-Phe-Val-Ala-Leu-Gly-COOH |

The preferred PTH34 and PTH38 fragments may be obtained commercially from suppliers such as Peninsula Laboratories, Inc., Belmont, Calif.; Sigma Chemical Co., St. Louis, Mo.; Bachem California, Torrance, Calif.; and others. Alternatively, the PTH fragments may be produced recombinantly by expression in cultured cells of recombinant DNA molecules encoding the desired fragment of the PTH molecule. Suitable recombinant expression systems and methods are well described in the literature. See, or example, Manniatis, *Molecular Cloning: A Laboratory Manual,* Cold Spring Harbor, N.Y., 1982. The DNA molecules which are expressed may themselves be synthetic or derived from a natural source. Synthetic polynucleoctides may be synthesized by well-known techniques, for example, single-stranded DNA fragments may be prepared by the phosphoraminite method first described by Beaucage and Carruthers (1981) Tett. Lett. 22:1859-1862. A double-stranded fragment may then be obtained either by synthesizing the complementary strand and annealing the strands together under appropriate conditions, or by adding the complementary strand using DNA polymerase with an appropriate primer sequence. The preparation of synthetic DNA sequences is conveniently accomplished using automated equipment available from suppliers, such as Applied Biosystems, Inc., Foster City, Calif.

The PTH fragments will be formulated in pharmaceutically acceptable compositions suitable for pulmonary or respiratory delivery to a mammalian host, usually a human host at risk of or suffering from osteoporosis. Particular formulations include dry powders, liquid solutions or suspensions suitable for nebulization, and propellant formulations suitable for use in metered dose inhalers (MDI's). The preparation of such formulations is well described in the patent, scientific, and medical literatures, and the following descriptions are intended to be exemplary only.

Dry powder formulations will typically comprise the PTH fragment in a dry, usually lyophilized, form with a particle size within a preferred range for deposition within the alveolar region of the lung, typically from 0.5 µm to 5 µm. Respirable powders of PTH fragments within the preferred size range can be produced by a variety of conventional techniques, such as jet-milling, spray-drying, solvent precipitation, and the like. Dry powders can then be administered to the patient in conventional dry powder inhalers (DPI's) that use the patient's inspiratory breath through the device to disperse the powder or in air-assisted devices that use an external power source to disperse the powder into an aerosol cloud. A particularly useful dry powder disperser is described in copending application Ser. No. 07/910,048, assigned to the assignee of the present invention, the full disclosure of which is incorporated herein by reference.

Dry powder devices typically require a powder mass in the range from about 1 mg to 10 mg to produce a single aerosolized dose ("puff"). Since the required dose of PTH fragment will generally be much lower than this amount, as discussed below, the PTH powder will typically be combined with a pharmaceutically acceptable dry bulking powder, with the PTH present usually at from about 1% to 10% by weight. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Typically, suitable buffers and salts may be used to stabilize the PTH fragments in solution prior to particle formation. Suitable buffers include phosphate, citrate, acetate, and tris-HCl, typically at concentrations from about 5 mM to 50 mM. Suitable salts include sodium chloride, sodium carbonate, calcium chloride, and the like. Other additives, such as chelating agents, peptidase inhibitors, and the like, which would facilitate the biological activity of the PTH fragment once it is dissolved within the lung would be appropriate. For example, ethylenediaminetetraacetic acid (ETDA) would be useful as a chelator for divalent cations which are peptidase cofactors.

Liquid formulations of PTH fragments for use in nebulizer systems can employ slightly acidic buffers (pH 4-6) with PTH concentrations of from about 1 mg/ml to 20 mg/ml. Suitable buffers include acetate, ascorbate, and citrate, at concentrations of 5 mM to 50 mM. These buffers can act as antioxidants, or other physiologically acceptable antioxidants can be added to protect free methionines in the PTH fragment against oxidation. Other components may be added to enhance or maintain chemical stability, including chelating agents, protease inhibitors, isotonic modifiers, inert gases, and the like. A preferred type of nebulizer suitable for delivering such liquid formulations is described in copending application Ser. No. 07/910,048, the disclosure of which has previously been incorporated herein by reference.

For use in MDI's, the PTH fragments of the present invention will be dissolved or suspended in a suitable aerosol propellant, such as chlorofluorocarbon (CFC) or hydrofluorocarbon (HFC). Suitable CFC's include trichloromonofluoromethane (propellant 11), dichlorotetrafluoromethane (propellant 114), and dichlorodifluoromethane, (propellant 12). Suitable HFC's include tetrafluoroethane (HFC-134a) and heptafluoropropane (HFC-227).

Preferably, for incorporation into the aerosol propellant, the PTH fragments of the present invention will be processed into respirable particles as described for the dry powder formulations. The particles are then suspended in the propellant, typically being coated with a surfactant to enhance their dispersion. Suitable surfactants include oleic acid, sorbitan trioleate, and various long chain diglycerides and phospholipids.

Such aerosol propellant formulations may further include a lower alcohol, such as ethanol (up to 30% by weight) and other additives to maintain or enhance chemical stability and physiological acceptability.

Pulmonary or respiratory administration of PTH fragments according to the present invention will be useful in the treatment of osteoporosis, where the PTH fragment will be administered in combination with vitamin D calcitonin, and/or dietary calcium supplements. Such treatment methods are well described in U.S. Pat. Nos. 4,698,328 and 4,833,125, the disclosures of which have previously been incorporated herein by reference.

The total aerosolized dosage of PTH fragment for the treatment of osteoporosis will typically be in range from about 100 µg to 2,000 µg per day, usually being in the range from about 250 µg to 1000 µg per day. Such dosages will result in a total systemic availability (i.e., amount which is delivered to the blood) in the range from about 50 µg to 500 µg per day, usually from 100 µg to 250 µg, per day. Precise dosages will, of course, vary depending on the activity of the particular PTH fragment or analog employed, and other known pharmacokinetic factors. Usually, the total dosage of PTH fragment will be delivered in a plurality of separate aerosolized doses, typically being at least two and, often being from three to ten, where each aerosolized bolus contains from 50 µg to 500 µg of the PTH fragment.

Pulmonary delivery of PTH fragments according to the methods of the present invention has been found to provide a desired pulsatile serum concentration profile. The pulsatile serum PTH fragment concentration profile will typically peak within 30 minutes after administration, with serum concentrations falling rapidly, typically to below 50% of maximum within 30 minutes of the peak and to below 25% within 60 minutes of the peak.

In the case of a dry powder formulation, a sufficient amount of dry bulking powder will be added so that a total dosage of PTH fragment within the above range can be achieved with one or more aerosolized boluses which are to be inhaled by the patient. Typically, the active PTH fragment will be present at from about 1% to 25% by weight of the powder, with aerosolized boluses including from 1 mg to 10 mg of the powder. Liquid formulations suitable for use in nebulizers typically have a concentration of the PTH fragment in the range from about 1 mg/ml to 20 mg/ml, with the total volume of nebulized liquid needed to deliver the bolus in the range from about 0.1 ml to 1 ml. The aerosol propellant formulations will be delivered by MDI at about 0.5 mg to 5 mg of PTH fragment per aerosol dose. Because of the inefficiencies of MDI devices, only a small portion, typically in the range of 5% to 20%, of the drug will reach the lungs. Thus, a sufficient amount of the PTH fragment can be delivered in from two to five aerosolized boluses, with about 1 mg of the PTH fragment in each of the boluses.

The following examples are offered by way of illustration, not by way of limitation.

EXPERIMENTAL

Materials and Methods

Recombinant human parathyroid hormone (PTH84) was obtained from Peninsula Laboratories, Inc., Belmont, Calif. (Lot No. 800929) A recombinant fragment (amino acids 1-34) of human parathyroid hormone (PTH34) was obtained from Sigma Chemical Co., St. Louis, Mo. (Lot No. 098F48052).

Rats (approximately 300-320 g) were obtained from Simonsone Labs, Gilroy, Calif.

PTH84 and PTH34 were administered to rats intravenously (IV) and intratracheally (IT) suspended in 100 μl of 20 mM citrate buffer, pH 5. Dosages were 5 μg for IV administration of PTH84, 100 μg for IT administration of PTH84, 25 μg for IV administration of PTH34, and 100 μg for IT administration of PTH34. IT administration was performed by making a one inch incision in the medial neck region and exposing the trachea. The polypeptide suspensions were injected into the trachea using a tuberculin syringe with a 30 gauge needle over approximately one minute. The head of the rat was held upright during the intratracheal injection and for one additional minute thereafter.

Rat serum was assayed for PTH34 at periodic intervals after PTH34 administration using a Nichols Instrument INS PTH assay kit which measures PTH34 with no cross-reactivity to PTH28-54, PTH44-68, and PTH53-84. Samples were diluted as necessary to obtain measurable concentrations.

Rat serum was assayed for PTH84 with Nichols Instrument Alegro assay kit for human PTH which measures PTH84 with no cross-reactivity with PTH34, PTH39-68, PTH44-68, PT53-84, and PTH39-84. Samples were diluted as necessary to obtain measurable concentrations.

Results

Figure 2:
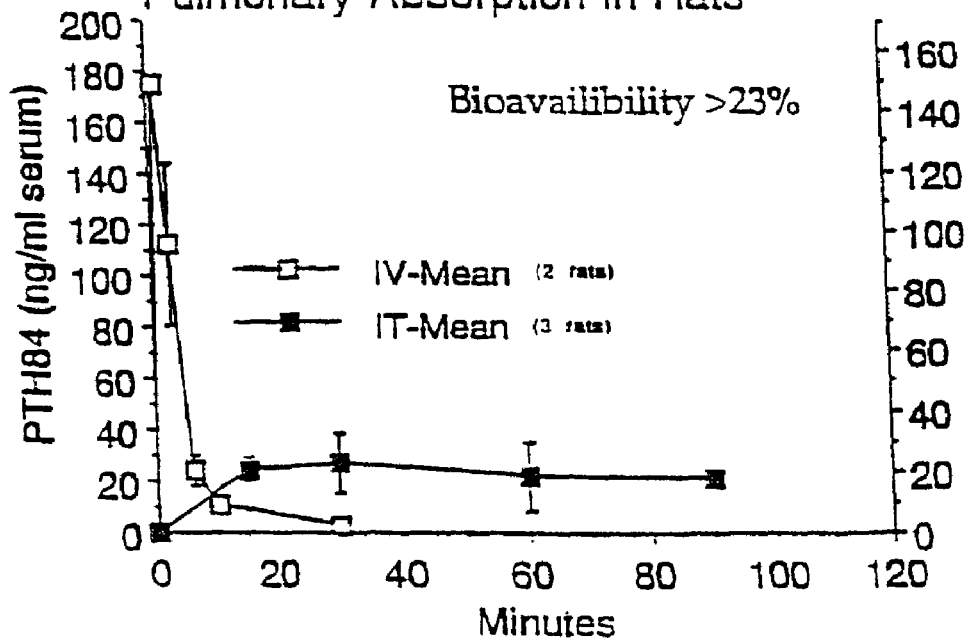
FIG. 2 is a grace illustrating the serum profile of PTH84 administered intravenously and intratracheally to rats, as described in detail in the Experimental section hereinafter.

The serum profiles of PTH34 and PTH84 in rats following IV and IT administration are shown in FIGS. 1 and 2, respectively. The absolute bioavailability of PTH34, which indicates the percentage of total administered hormone that got into the blood, was about 40%. The absorption profile of PTH34 exhibited a spike at 15 minutes with activity diminishing rapidly thereafter. This is similar to the profile seen after subcutaneous injection. In contract, PTH84 at the same intratracheal dose, exhibited a very different absorption profile. Instead of a spike, a plateau in serum levels occurred that did not diminish significantly during the 90 minutes of the experiment. The bioavailability of PTH84 at 90 minutes was about 23% (as measured by the truncated area under the curve up to 90 minutes), but the slow sustained release absorption profile suggests that serum levels would have persisted for longer times.

Although the foregoing invention has been described in detail for purposes of clarity of understanding, it will be obvious that certain modifications may be practiced within the scope of the appended claims.

What is claimed is:

1. A therapeutic composition in solid dose form comprising a bulking agent and an N-terminal peptide fragment of parathyroid hormone (PTH) as a bioactive agent, wherein said composition is a powder suitable for administration by inhalation, said bulking agent is selected from the group consisting of sucrose, lactose, trehalose, dextran and maltotriose, and said powder has a particle size between 0.5 μm to 5 μm.

2. The composition according to claim 1, wherein said peptide fragment consists of the first 34 amino acids of SEQ ID NO: 1.

3. The composition according to claim 1, wherein said peptide fragment consists of the first 34 to 38 amino acids of SEQ ID NO: 1.

4. The composition according to claim 1, further comprising an additive to maintain or enhance chemical stability and physiological acceptability.

5. The composition according to claim 4, wherein the additive is a peptidase inhibitor.

6. The composition according to claim 4, wherein the additive is a chelating agent.

* * * * *